United States Patent [19]
Kellogg

[11] Patent Number: 5,968,060
[45] Date of Patent: *Oct. 19, 1999

[54] ULTRASONIC INTERLOCK AND METHOD OF USING THE SAME

[75] Inventor: Scott Kellogg, Esmond, R.I.

[73] Assignee: Ethicon Endo-Surgery, Inc., Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/808,638

[22] Filed: Feb. 28, 1997

[51] Int. Cl.$^6$ .................................................. A61B 17/34
[52] U.S. Cl. ........................................ 606/169; 606/185
[58] Field of Search ...................... 606/169, 185, 606/128; 433/119, 86; 601/2; 228/1.1; 604/22

[56] References Cited

U.S. PATENT DOCUMENTS

| | | | |
|---|---|---|---|
| Re. 30,536 | 3/1981 | Perreaux, Jr. ................. | 433/86 |
| 2,845,072 | 7/1958 | Shafer . | |
| 2,874,470 | 2/1959 | Richards ......................... | 32/58 |
| 3,053,124 | 9/1962 | Balamuth et al. . | |
| 3,075,288 | 1/1963 | Balamuth et al. ............... | 32/58 |
| 3,076,904 | 2/1963 | Kleesattel et al. ............. | 310/26 |
| 3,213,537 | 10/1965 | Balamuth et al. .............. | 32/28 |
| 3,368,280 | 2/1968 | Fridman et al. ................ | 32/58 |
| 3,375,583 | 4/1968 | Blank et al. .................... | 32/26 |
| 3,433,226 | 3/1969 | Boyd . | |
| 3,488,851 | 1/1970 | Haydu ............................ | 32/58 |
| 3,489,930 | 1/1970 | Shoh .............................. | 310/8.1 |
| 3,526,036 | 9/1970 | Goof .............................. | 32/28 |
| 3,526,792 | 9/1970 | Shoh .............................. | 310/8.1 |
| 3,589,012 | 6/1971 | Richman ......................... | 32/58 |
| 3,589,363 | 6/1971 | Banko et al. .................. | 128/276 |
| 3,593,425 | 7/1971 | Robinson ........................ | 32/58 |
| 3,636,943 | 1/1972 | Balamuth . | |
| 3,636,947 | 1/1972 | Balamuth ....................... | 128/66 |
| 3,654,502 | 4/1972 | Carmona et al. ............... | 310/26 |
| 3,654,540 | 4/1972 | Honig et al. ................... | 318/118 |
| 3,657,056 | 4/1972 | Winston et al. . | |

(List continued on next page.)

FOREIGN PATENT DOCUMENTS

| | | |
|---|---|---|
| 1098003 | 9/1977 | Canada . |
| 0 495 634 A2 | 1/1992 | European Pat. Off. . |
| 0 624 346 A2 | 5/1994 | European Pat. Off. . |
| 0 624 346 A3 | 5/1994 | European Pat. Off. . |
| 2032501 | 7/1970 | Germany . |

(List continued on next page.)

OTHER PUBLICATIONS

Cooper LaserSonics, Inc., Ultrasonic Surgucal Aspirator NS–100 Operator Manual, 1984, pp. 12, 13, 16, 17, and 29–33.

Primary Examiner—Michael H. Thaler
Attorney, Agent, or Firm—Verne E. Kreger

[57] ABSTRACT

An ultrasonic surgical device includes a transducer assembly adapted to vibrate at an ultrasonic frequency in response to electrical energy. A transmission component having a transmission component adapted to receive ultrasonic vibration from the transducer assembly and to transmit the ultrasonic vibration from a first end to a second end. A braking device is configured to apply a force to the outer surface of the transmission component to dampen the ultrasonic vibration being transmitted from the first end of the transmission rod to the second end of the transmission rod. A method of inserting a trocar cannula into tissue of a patient is also provided. The method includes the steps of providing an ultrasonic trocar obturator having an ultrasonic waveguide including an end effector at a distal end thereof, positioning the trocar obturator within a trocar cannula, positioning the trocar obturator in contact with a wall of said body cavity, and ultrasonicly vibrating the end effector to create a penetration opening. The method further includes advancing the ultrasonic obturator into said penetration opening, detecting when penetration has been completed, applying a braking member to the obturator to dampen the ultrasonic vibration of the end effector, and advancing the trocar cannula into the penetration opening.

6 Claims, 5 Drawing Sheets

U.S. PATENT DOCUMENTS

| | | | |
|---|---|---|---|
| 3,703,037 | 11/1972 | Robinson | 32/58 |
| 3,792,701 | 2/1974 | Kloz et al. . | |
| 3,809,977 | 5/1974 | Balamuth et al. | 318/116 |
| 3,819,961 | 6/1974 | Bourgeois et al. . | |
| 3,842,340 | 10/1974 | Brandquist . | |
| 3,930,173 | 12/1975 | Banko | 310/26 |
| 3,956,826 | 5/1976 | Perdreaux, Jr. | 32/58 |
| 3,967,143 | 6/1976 | Watanabe et al. . | |
| 4,156,157 | 5/1979 | Mabille | 310/316 |
| 4,169,984 | 10/1979 | Parisi . | |
| 4,175,242 | 11/1979 | Kleinschmidt | 310/316 |
| 4,188,952 | 2/1980 | Loschilov et al. | 128/305 |
| 4,223,676 | 9/1980 | Wuchinich et al. . | |
| 4,227,110 | 10/1980 | Douglas et al. | 310/316 |
| 4,370,131 | 1/1983 | Banko | 433/86 |
| 4,371,816 | 2/1983 | Wieser | 318/116 |
| 4,375,961 | 3/1983 | Brooks . | |
| 4,406,284 | 9/1983 | Banko | 128/303 |
| 4,491,132 | 1/1985 | Aikins | 128/305 |
| 4,492,574 | 1/1985 | Warrin et al. | 433/81 |
| 4,522,206 | 6/1985 | Whipple et al. . | |
| 4,655,216 | 4/1987 | Tischer . | |
| 4,723,545 | 2/1988 | Nixon et al. . | |
| 4,750,488 | 6/1988 | Wuchinich et al. | 128/303 |
| 4,808,153 | 2/1989 | Parisi | 604/22 |
| 4,816,018 | 3/1989 | Parisi | 604/22 |
| 4,820,152 | 4/1989 | Warrin et al. | 433/86 |
| 4,825,865 | 5/1989 | Zelman . | |
| 4,832,683 | 5/1989 | Idemoto et al. . | |
| 4,867,141 | 9/1989 | Nakada et al. | 128/24 |
| 4,870,953 | 10/1989 | DonMicheal et al. | 128/24 |
| 4,884,334 | 12/1989 | Houser et al. | 228/1.1 X |
| 4,897,079 | 1/1990 | Zaleski et al. | 604/22 |
| 4,920,954 | 5/1990 | Alliger et al. | 128/24 |
| 4,922,902 | 5/1990 | Wuchinich et al. | 604/22 |
| 4,931,047 | 6/1990 | Broadwin et al. | 604/22 |
| 4,936,281 | 6/1990 | Stasz | 128/660.03 |
| 4,974,590 | 12/1990 | Saito | 128/662.06 |
| 4,979,952 | 12/1990 | Kubota et al. | 606/169 |
| 5,011,471 | 4/1991 | Miyazaki et al. | 604/22 |
| 5,026,387 | 6/1991 | Thomas | 606/169 |
| 5,047,043 | 9/1991 | Kubota et al. | 606/169 |
| 5,057,119 | 10/1991 | Clark et al. | 606/169 |
| 5,059,210 | 10/1991 | Clark et al. | 606/169 |
| 5,069,664 | 12/1991 | Guess et al. | 604/22 |
| 5,112,300 | 5/1992 | Ureche | 604/22 |
| 5,123,903 | 6/1992 | Quaid et al. | 604/22 |
| 5,151,084 | 9/1992 | Khek | 604/22 |
| 5,151,085 | 9/1992 | Sakuri et al. | 604/22 |
| 5,160,317 | 11/1992 | Costin | 604/22 |
| 5,167,725 | 12/1992 | Clark et al. | 428/680 |
| 5,180,363 | 1/1993 | Idemoto et al. | 202/32 |
| 5,190,517 | 3/1993 | Zieve et al. | 604/22 |
| 5,248,296 | 9/1993 | Alliger | 609/22 |
| 5,263,957 | 11/1993 | Davison . | |
| 5,269,309 | 12/1993 | Fort et al. | 128/661.01 |
| 5,322,055 | 6/1994 | Davison et al. . | |
| 5,324,299 | 6/1994 | Davison et al. . | |
| 5,342,292 | 8/1994 | Nita et al. | 604/22 |
| 5,344,420 | 9/1994 | Hilal et al. | 606/28 |
| 5,346,502 | 9/1994 | Estabrook et al. | 606/169 |
| 5,380,274 | 1/1995 | Nita | 604/22 |
| 5,397,293 | 3/1995 | Alliger et al. . | |
| 5,425,704 | 6/1995 | Sakurai et al. | 604/22 |
| 5,438,554 | 8/1995 | Seyed-Bolorforosh et al. | 367/140 |
| 5,449,370 | 9/1995 | Vaitekunas | 606/169 |
| 5,472,447 | 12/1995 | Abrams et al. | 606/169 |
| 5,507,738 | 4/1996 | Ciervo | 606/1 |
| 5,507,743 | 4/1996 | Edwards et al. | 606/41 |
| 5,509,916 | 4/1996 | Taylor | 606/13 |
| 5,526,815 | 6/1996 | Granz et al. | 128/660.03 |
| 5,540,656 | 7/1996 | Pflueger et al. | 604/22 |
| 5,542,917 | 8/1996 | Nita et al. | 604/22 |
| 5,546,947 | 8/1996 | Yagami et al. | 128/662.06 |
| 5,562,609 | 10/1996 | Brumbach | 604/22 |
| 5,562,610 | 10/1996 | Brumbach | 604/22 |
| 5,582,588 | 12/1996 | Sakurai et al. | 604/22 |
| 5,606,974 | 3/1997 | Castellano et al. | 128/662.06 |
| 5,628,743 | 5/1997 | Cimino | 606/1 |
| 5,634,466 | 6/1997 | Gruner . | |
| 5,653,721 | 8/1997 | Knodel et al. . | |
| 5,688,235 | 11/1997 | Sakurai et al. . | |

FOREIGN PATENT DOCUMENTS

| | | |
|---|---|---|
| 76-18881 | 6/1976 | Germany . |
| 77-05-069 | 2/1977 | Germany . |
| 29 22 239 | 5/1979 | Germany . |
| 37 07 921 A1 | 3/1987 | Germany . |
| 19534618 A1 | 9/1995 | Germany . |
| 56-108085 | of 1981 | Japan . |
| 56-38931 | of 1981 | Japan . |
| 61-265136 | of 1986 | Japan . |
| 61-128954 | 6/1986 | Japan . |
| 63-61609 | 3/1988 | Japan . |
| 63-61609 | 4/1988 | Japan . |
| 63-61609 | 11/1988 | Japan . |
| 2-99049 | of 1990 | Japan . |
| 8-275948 | 10/1996 | Japan . |
| 8-275949 | 10/1996 | Japan . |
| 8-275951 | 10/1996 | Japan . |
| 1388002 A1 | 4/1988 | Russian Federation . |
| WO 91/13591 | 3/1991 | WIPO . |
| WO 92/02658 | 7/1991 | WIPO . |
| 0 495 634 A3 | 1/1992 | WIPO . |
| WO 92/14514 | 2/1992 | WIPO . |
| WO 93/14708 | 1/1993 | WIPO . |
| WO 93/16646 | 1/1993 | WIPO . |
| WO 96/29935 | 4/1996 | WIPO . |
| WO 96/34561 | 5/1996 | WIPO . |

ULTRASONIC INTERLOCK AND METHOD OF USING THE SAME

FIELD OF THE INVENTION

The present invention relates generally to an ultrasonic devices, and more particularly to an ultrasonic interlock or braking mechanism that can dampen the ultrasonic vibration of a transmission component.

BACKGROUND OF THE INVENTION

Minimally invasive endoscopic surgical procedures have become increasingly widespread in view of the reduced trauma for patients, and their highly cost-effective nature. For such procedures, a trocar assembly is typically employed for effecting penetration of the wall of a body cavity of the patient. A typical trocar assembly includes an outer tubular cannula, and an inner tissue-piercing obturator having a puncturing tip. For use, the trocar assembly is positioned so that the obturator can be advanced to form an opening in the wall of the body cavity with the puncturing tip, and the cannula thereafter inserted through the opening. The obturator is then removed from within the cannula, with the cannula thereafter providing access for insertion of surgical instruments and other devices related to the surgical procedure to be performed.

Many trocar assemblies have a retractable or removable shield that can cover the puncturing tip of the obturator, thus covering the tissue-piercing portion of the assembly. When the trocar assembly is positioned for puncturing the body cavity of a patient, the shield can be retracted to expose the puncturing tip to pierce the wall of the body cavity. Once the body cavity has been pierced, the shield re-covers the puncturing tip of the obturator. For example, in abdominal surgery, when the peritoneal cavity is reached, the shield covers the puncturing tip of the obturator.

Use of ultrasonic surgical instruments is also becoming increasingly widespread by virtue of the unique performance characteristics of such devices. Depending upon specific instrument configuration and operational parameters, such devices can provide substantially simultaneous cutting of tissue and hemostasis, again desirably minimizing patient trauma.

U.S. Pat. No. 5,449,370, hereby incorporated by reference, discloses an ultrasonic trocar assembly including an ultrasonic obturator configured to effect ultrasonic penetration of the wall of a body cavity for subsequent introduction of a tubular cannula of the trocar assembly. The obturator of the trocar assembly is provided with a blunt or rounded tip for minimizing patient trauma attendant to penetration of the body cavity. When the obturator penetrates the tissue of a patient, a feedback mechanism shuts off or reduces the ultrasonic energy delivered to the obturator.

The present invention is directed to an interlock or braking mechanism that mechanically dampens the ultrasonic energy delivered to a transmission component.

SUMMARY OF THE INVENTION

An ultrasonic interlock embodying the principles of the present invention is provided to mechanically dampen the vibration of a transmission component. The interlock engages the periphery of a transmission component to dampen, arrest or reduce the vibration of the transmission component. When the interlock is engaged with the transmission component, a force is applied to the transmission component to prevent the ultrasonic energy from being transmitted through the transmission component.

The interlock can also engage the transmission component to prevent inadvertent delivery of ultrasonic energy. The interlock may be utilized on any suitable ultrasonic device or ultrasonic surgical device, such as, for example, an ultrasonic scalpel and an ultrasonic trocar.

An ultrasonic surgical device in accordance with the present invention includes a transducer assembly adapted to vibrate at an ultrasonic frequency in response to electrical energy. A transmission component is adapted to receive ultrasonic vibration from the transducer assembly and to transmit the ultrasonic vibration from a first end to a second end. A braking device is configured to apply a force to the outer surface of the transmission component to dampen the ultrasonic vibration being transmitted from the first end of the transmission rod to the second end of the transmission rod.

A method in accordance with the present invention includes the steps of providing an ultrasonic trocar obturator having an ultrasonic waveguide including an end effector at a distal end thereof, positioning the trocar obturator within a trocar cannula, positioning the trocar obturator in contact with a wall of said body cavity, and ultrasonicly vibrating the end effector to create a penetration opening. The method also includes the steps of advancing the ultrasonic obturator into said penetration opening, detecting when penetration has been completed, and applying a braking member to the obturator to dampen the ultrasonic vibration of the end effector and advancing the trocar cannula into the penetration opening.

Other features and advantages of the present invention will become readily apparent from the following detailed description, the accompanying drawings, and the appended claims.

DETAILED DESCRIPTION OF THE PREFERRED EMBODIMENTS

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiments illustrated.

Figure 1:
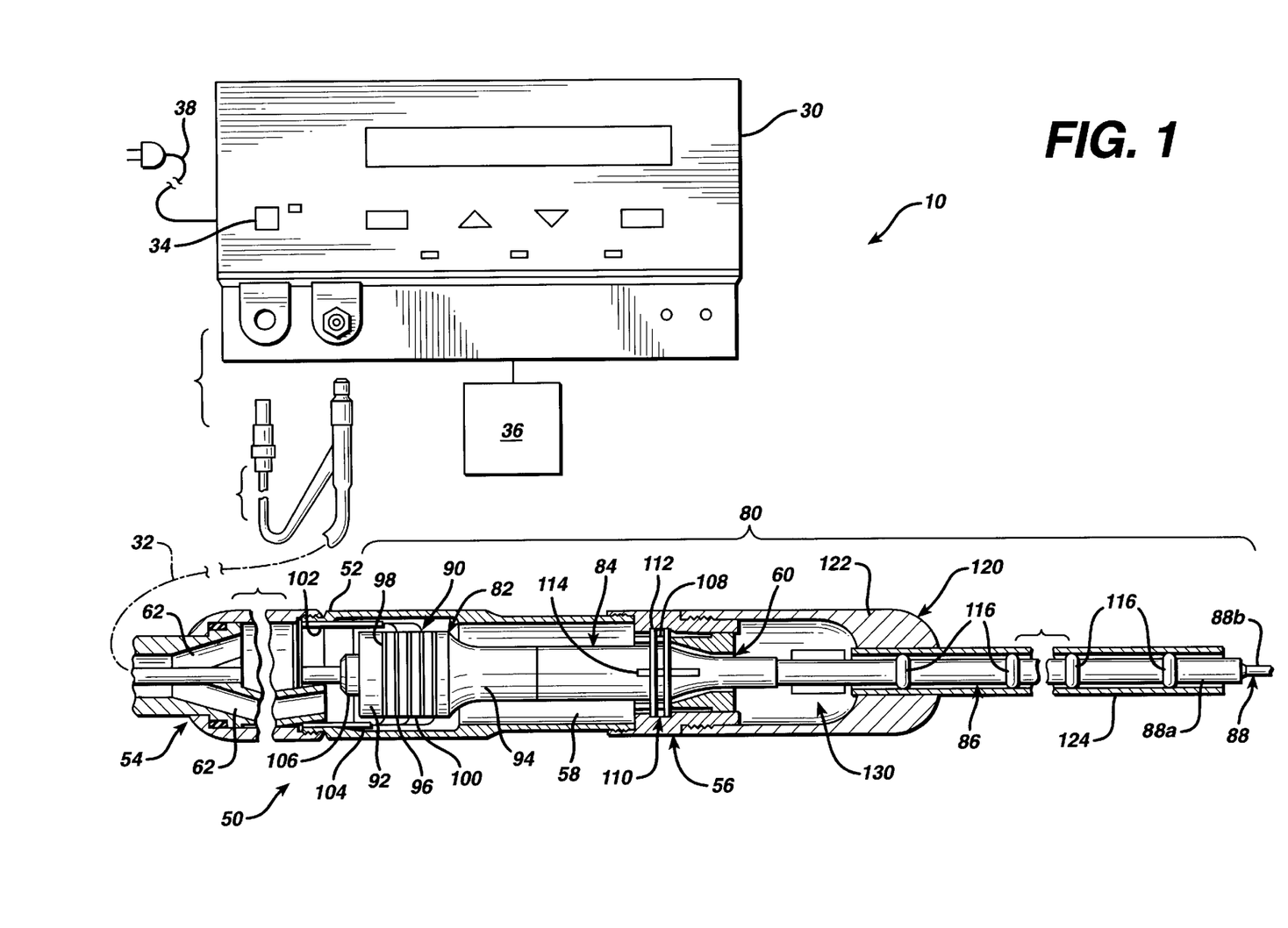
FIG. 1 is a fragmentary view and in partial cross-section of an embodiment of a surgical system according to the present invention.

Referring now to FIG. 1, a presently preferred embodiment of a surgical system 10 is illustrated. The surgical system 10 generally includes a generator 30, a handpiece assembly 50, an acoustic or transmission assembly 80, and an interlock or braking mechanism 130. The generator 30 sends an electrical signal through a cable 32 at a selected amplitude, frequency, and phase determined by a control system of the generator 30. As will be firer described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. An end effector 88 at the distal end of the acoustic assembly 80 is placed in contact with tissue of the patient to transfer the ultrasonic energy to the tissue. The cells of the tissue in contact with the end effector 88 of the acoustic assembly 80 will move with the end effector 88 and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 in the surgical system 10 tends to focus the vibrational energy of the system 10 onto tissue in contact with the end effector 88, intensifying and localizing thermal and mechanical energy delivery.

As illustrated in FIG. 1, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy may be continuously applied by the generator 30 to a transducer assembly 82 of the acoustic assembly 80 until the braking mechanism or interlock 130 is applied as described below, or the triggering mechanism 36 is deactivated. A phase locked loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electrical current supplied to the acoustic assembly 80 at a preselected constant level in order to achieve substantially constant vibrational amplitude at the end effector 88 of the acoustic assembly 80. The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 may be controlled by, for example, controlling the amplitude of the electrical signal applied to the transducer assembly 82 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. The generator 30 may be any suitable generator, such as Model No. GENO1, available from Ethicon Endo-Surgery, Inc.

Referring still to FIG. 1, the handpiece assembly 50 includes a multi-piece housing or outer casing 52 adapted to isolate the operator from the vibrations of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e. high impact polystyrene or polypropylene). A suitable handpiece assembly 50 is Model No. HP050, available from Ethicon Endo-Surgery, Inc.

As illustrated in FIG. 1, the handpiece assembly 50 generally includes a proximal end 54, a distal end 56, and centrally disposed axial opening or cavity 58 extending longitudinally therein. The distal end 56 of the handpiece assembly 50 includes an opening 60 configured to allow the acoustic assembly 80 of the surgical system 10 to extend therethrough, and the proximal end 54 of the handpiece assembly 50 is coupled to the generator 30 by a cable 32. The cable 32 may include ducts or vents 62 to allow air to be introduced into the handpiece assembly 50 to cool the transducer assembly 82 of the acoustic assembly 80.

Referring still to FIG. 1, the acoustic assembly 80 generally includes a transducer stack or assembly 82 and a transmission component. The transmission component may include a mounting device 84, a transmission rod or waveguide 86, and an end effector or applicator 88. The transducer assembly 82, mounting device 84, transmission rod 86, and the end effector 88 are preferably acoustically tuned such that the length of each component is an integral number of one-half system wavelengths ($n\lambda/2$) where the system wavelength λ is the wavelength of a preselected or operating longitudinal vibration frequency f of the acoustic assembly 80. It is also contemplated that the acoustic assembly 80 may incorporate any suitable arrangement of acoustic elements. For example, the acoustic assembly 80 may comprise a transducer assembly and an end effector (i.e., the acoustic assembly 80 may be configured without a mounting device and a transmission rod).

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength (λ/4).

As shown in FIG. 1, the transducer assembly 82 of the acoustic assembly 80, which is known as a "Langevin stack", generally includes a transduction portion 90, a first resonator 92, and a second resonator 94. The transducer assembly 82 is preferably an integral number of one-half system wavelengths (nλ/2) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulus of elasticity of material used in the resonators 92 and 94, and the fundamental frequency of the transducer assembly 82. The second resonator 94 may be tapered inwardly from its proximal end to its distal end to amplify the ultrasonic vibration amplitude.

The transduction portion 90 of the transducer assembly 82 preferably comprises a piezoelectric section of alternating positive electrodes 96 and negative electrodes 98, with piezoelectric elements 100 alternating between the electrodes 96 and 98. The piezoelectric elements 100 may be fabricated from any suitable material, such as, for example, lead zirconate-titante, lead meta-niobate, lead titanate, or ceramic piezoelectric crystal material. Each of the positive electrodes 96, negative electrodes 98, and piezoelectric elements 100 may have a bore extending through the center. The positive and negative electrodes 96 and 98 are electrically coupled to a wires 102 and 104, respectfully. Wires 102 and 104 transmit electrical signal from the generator 30 to electrodes 96 and 98.

As shown in FIG. 1, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within te material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic assembly 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection near an antinode. (For purposes of this disclosure, the term "near" is defined as "exactly at" or "in close proximity to".) It is contemplated that the mounting device 84 may be attached to the second resonator 94 by any suitable means, and that the second resonator 94 and mounting device 84 may be formed as a single or unitary component.

The mounting device 84 is connected or mounted to the housing 52 of the handpiece assembly 50 near a node. The mounting device 84 may include an integral ring 108 disposed around its periphery. The integral ring 108 is preferably disposed in an annular groove 110 formed in the housing 52 of the handpiece assembly 50 to mount the mounting device 84 to the housing 58. A compliant member or material 112, such as a pair of silicone O-rings attached by stand-offs, may be placed between the annular groove 110 of the housing 52 and the integral ring 108 of the mounting device 84 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction 90 degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel.

The mounting device 84 is preferably configured to amplify the ultrasonic vibration amplitude that is transmitted through the acoustic assembly 80 to the distal end of the end effector 88. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 may be any suitable shape, such as a stepped horn, a conical horn, an exponential horn, or the like.

The distal end of the mounting device 84 is coupled to the proximal end of the transmission rod 86. It is contemplated that the transmission rod 86 be attached to the mounting device 84 by any suitable means, such as, for example, an internal threaded connection. The mounting device 84 is preferably coupled to the transmission rod 86 near an antinode.

The transmission rod 86 may, for example, have a length substantially equal to an integer number of one-half system wavelengths (nλ/2). The transmission rod 86 may be preferably fabricated from a solid core shaft constructed out of material which propagates ultrasonic energy efficiently, such as titanium alloy (i.e., Ti-6Al-4V) or an aluminum alloy. It is contemplated that the transmission rod 86 may be fabricated from any suitable material. The transmission rod 86 may also amplify the mechanical vibrations transmitted through the transmission rod 86 to the end effector 88 as is well known in the art.

As illustrated in FIG. 1, the transmission rod 86 includes stabilizing silicone rings or compliant supports 116 positioned at a plurality of nodes. The silicone rings 116 dampen undesirable vibration and isolate the ultrasonic energy from a removable sheath 120 assuring the flow of ultrasonic energy in a longitudinal direction to the distal end of the end effector 88 with maximum efficiency.

The removable sheath 120 is coupled to the distal end 56 of the handpiece assembly 50. The sheath 120 generally includes an adapter or nose cone 122 and an elongated tubular member 124. The elongated tubular member 124 extends from the adapter 122 and has an opening extending longitudinally therethrough. The sheath 120 may be threaded or snapped onto the distal end of the housing 52. The transmission rod 86 of the acoustic assembly 80 extends through the opening of the tubular member 124 and, the silicone rings 116 isolate the transmission rod 86 from the tubular member 124.

The adapter 122 of the sheath 120 is preferably constructed from Ultem®, and the tubular member 124 is fabricated from stainless steel. Alternatively, the transmission rod 86 may have polymeric material that surrounds the transmission rod 86 to isolate it from outside contact.

The distal end of the transmission rod 86 may be coupled to the proximal end of the end effector 88 by an internal threaded connection, preferably at or near an antinode. It is contemplated that the end effector 88 may be attached to the transmission rod 86 by any suitable means, such as a welded joint or the like. Although the end effector 88 may be detachable from the transmission rod 86, it is also contemplated that the end effector 88 and transmission rod 86 may be formed as a single unit.

The end effector 88 may have a distal region 88b having a smaller cross-section area than a proximal region 88a thereof, thereby forming a vibrational amplitude step-up junction. The step-up junction acts as velocity transformer as known in the art, increasing the magnitude of the ultrasonic vibration transmitted from the proximal region 88a to the distal region 88b of the end effector 88.

The end effector 88 preferably has a length substantially equal to an integral multiple of one-half system wavelengths (nλ/2). The end effector 88 is disposed at an antinode in order to produce the maximum longitudinal deflection of the distal end. When the transducer assembly 82 is energized, the distal end of the end effector 88 is configured to move longitudinally in the range of, for example, approximately 10 to 500 microns peak-to-peak, and preferably in the range of about 30 to 100 microns at a predetermined vibrational frequency, and most preferably at about 90 microns.

The end effector 88 is preferably made from a solid core shaft constructed of material which propagates ultrasonic energy, such as a titanium alloy (i.e., Ti-6Al-4V) or an aluminum alloy. It will be recognized that the end effector 88 may be fabricated from other suitable materials. It is also contemplated that the end effector 88 may have a surface treatment to improve the delivery of energy and desired tissue effect. For example, the end effector 88 may be micro-finished, coated, plated, etched, grit-blasted, roughened or scored to enhance coagulation in tissue. Additionally, the end effector 88 may be sharpened or shaped to enhance its energy transmission characteristics. For example, the end effector 88 may be blade shaped, hook shaped, or ball shaped.

Figure 2:
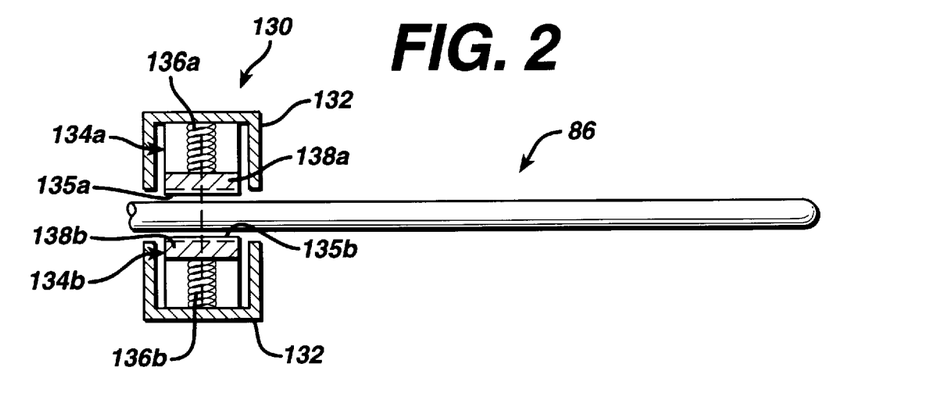
FIG. 2 is a diagrammatical view of an interlock of the surgical system of FIG. 1 in a retracted position.
Figure 3:
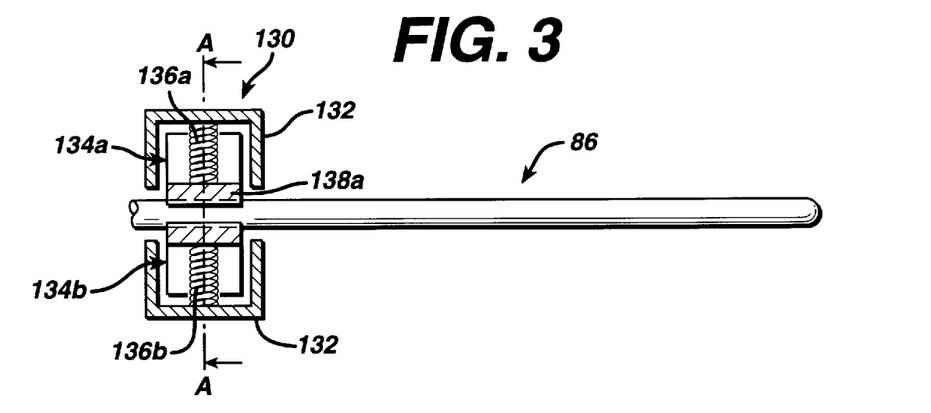
FIG. 3 is a diagrammatical view of the interlock of FIG. 2 in an engaging position.
Figure 3A:
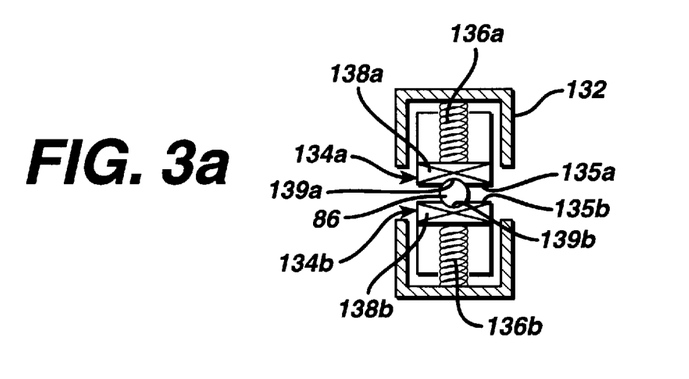
FIG. 3a is a cross-sectional view of the interlock of FIG. 3 about line A—A.

Referring now to FIGS. 2, 3, and 3a, diagrammatic views of the interlock 130 of the surgical system 10 are illustrated. The interlock 130 is preferably positioned near the proximal end of the transmission member 86. It is contemplated that the interlock 130 may be positioned at any suitable position along the acoustic assembly 80. For example and without limitation, the interlock 130 may be positioned to contact the transducer assembly 82, the mounting device 84, or the end effector 88. It will also be recognized that a plurality of interlocks may be positioned along the acoustic assembly.

The interlock 130 of the surgical system 10 may be coupled to or incorporated into the handpiece assembly or the removable sheath as would be recognized by those skilled in the art. As shown in FIGS. 2, 3 and 3a, the interlock 130 includes a housing 132 and braking members 134a and 134b. The braking member 134a and 134b are preferably mounted on opposing sides of the transmission rod 86. It will be recognized that the interlock 130 may have any suitable number of braking members 134a and 134b, (i.e. 1 to 6) and may be mounted in any suitable arrangement to engage the transmission rod 86.

The interlock 130 may be moved manually or automatically. For example, the interlock 130 may be forced against the acoustical assembly when a user manually depresses the braking members 134a and 134b to dampen, reduce and/or arrest ultrasonic energy. Alternatively, the interlock 130 may be activated to dampen, reduce and/or arrest the ultrasonic energy when the end effector 88 has penetrated a desired tissue of a patient (i.e., a patient abdominal wall or the inner wall of a heart).

A detection device may be utilized to determine when to cease the motion of the end effector 88. The detection mechanism may be used to sense when the end effector 88 has penetrated the tissue at which point the interlock 130 may be activated to dampen the ultrasonic energy delivered to the end effector 88. The detection mechanism may include a mechanical load change sensor that detects when the end effector 88 has adequate tissue penetration and mechanically triggers the activation of the braking members 134a and 134b. It is contemplated that the interlock 130 may be activated when an impedance level corresponding to adequate penetration is sensed or detected. For example, U.S. Pat. No. 5,449,370 discloses a feedback mechanism that senses variation in the load or impedance of the end effector. It will be recognized that the interlock 130 may also be triggered when a user depresses a button or switch incorporated into the generator, handpiece assembly or the removable sheath, or the interlock 130 may be activated to actuate the assembly by any suitable means, such as, for example, a mechanical trigger.

The braking members 134a and 134b of the interlock 130 preferably include resilient members 136a and 136b and brake pads 138a and 138b. The brake pads 138a and 138b are preferably of a rectangular configuration. It is also contemplated that the brake pads 138a and 138b may be any shape or size. The brake pads 138a and 138b may comprises a single pad or may comprises a plurality of pads.

The braking pads 138a and 138b preferably have a high operating temperature and are constructed so that they will not scratch or gouge the transmission rod 86. The braking pads 138a and 138b may be manufactured from polytetra fluoroethylene (PTFE/TFE) or fluorinated ethylenepropylene (FEP). It will be recognized that the braking pad 138a and 138b may be any suitable material known in the art.

The braking pads 138a and 138b each preferably include a front surface 135a and 135b, respectively, that conforms to the periphery of the transmission rod 86. As shown in FIG. 3a, the front surfaces 135a and 135b each have a concave surface or groove 139a and 139b, respectively, to engage the transmission rod 86. It is contemplated that the front surface of the braking members 134a and 134b may have any desirable configuration and may be substantially flat. It is also contemplated that the braking pads 138a and 138b may be carried by backing plates that hold the braking pads.

The resilient members 136a and 136b are attached to the rear of the braking pads 138a and 138b. The resilient members 136a and 136b bias the braking pads 138a and 138b towards the transmission rod 86. Preferably, the resilient members 136a and 136b comprise springs. It is also contemplated that the resilient members 136a and 136b may comprise any suitable mechanism to bias the braking pads 138a and 138b, such as, for example, a solenoid, a pneumatic piston, etc.

The braking pads 138a and 138b of the interlock 130 can be adapted to engage the periphery of the acoustic assembly at a suitable point or location to dampen, reduce or arrest the ultrasonic vibration of the transmission rod and/or end effector. The braking pads 138a and 138b are preferably applied to the acoustic assembly in the vicinity of an antinode.

In use, the braking members 134a and 134b of the interlock 130 are in a retracted or disengaged position as shown in FIG. 2. In this position, the braking pads 138a and 138b are held at a predetermined distance away from the transmission rod 86. When the ultrasonic vibration of the transmission rod is desired to be dampened or stopped, the braking members 134a and 134b are pushed against the transmission rod as shown in FIG. 3. When the brake pads 138a and 138b of the brake members 134a and 134b are depressed against the transmission rod, the impedance of the ultrasonic transmission rod is sufficiently increased so that the generator 30 can no longer lock onto a resonant frequency of the transmission rod and produce an adequate drive signal. As a result, the motion of the transmission rod stops and the generator reports a continuous tone.

Figure 4:
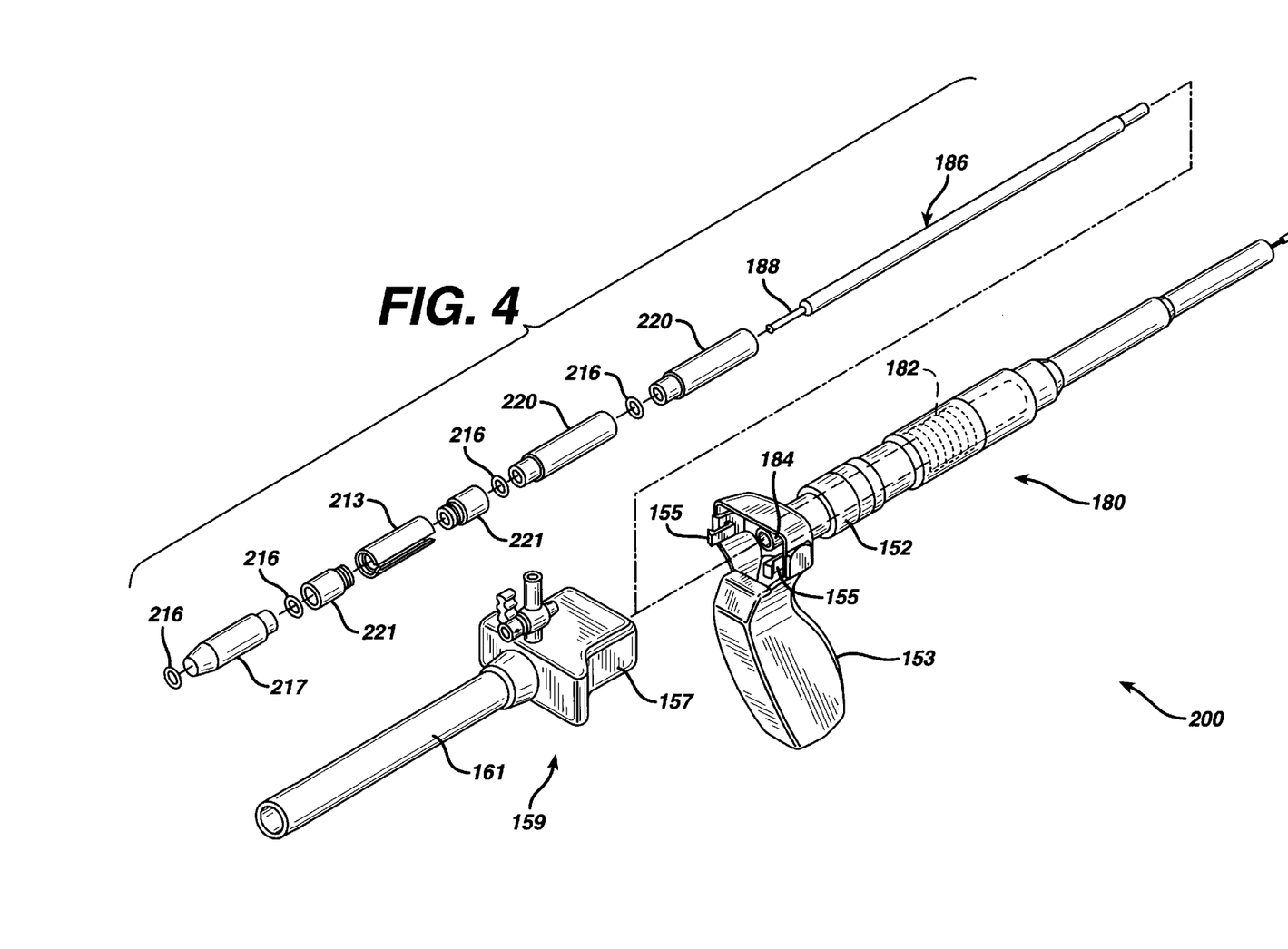
FIG. 4 is an exploded view of an ultrasonic trocar assembly.

Referring now to FIG. 4, an exemplary ultrasonic trocar assembly 200 is illustrated. It will be understood that the ultrasonic trocar assembly 200 can be configured, in many respects, in accordance with surgical system 10 as described above. Thus, for purposes of the present disclosure, the trocar assembly 200 is configured in accordance with the surgical system 10, as described above, except as otherwise note. The ultrasonic trocar assembly 200 differs from the surgical system 10 illustrated in FIG. 1 in that the trocar assembly 200 includes an ultrasonic obturator useable in conjunction with a tubular trocar cannula. U.S. Pat. No. 5,449,370, hereby incorporated by reference, discloses an ultrasonic trocar assembly including an ultrasonic obturator configured to effect ultrasonic penetration of the wall of a body cavity for subsequent introduction of a tubular cannula of the trocar assembly.

As shown in FIG. 4, the trocar assembly 200 includes an acoustic assembly configured as an obturator 180, which in many respects corresponds in construction and function to the previously described acoustic assembly of surgical system 10. Components of the trocar assembly 200 which generally correspond to those components of surgical system 10 are designated by like reference numerals in the one-hundred and two-hundred series.

The obturator 180 of the trocar assembly 200 includes a housing 152 having positioned therein a transducer assembly 182 configured in accordance with previously-described transducer assembly 82. To facilitate manipulation of the obturator 180, a handgrip 153 is preferably provided which is joined to the housing 152 of the trocar assembly. A pair of manually operable locking clips 155 are preferably provided on the upper portion of the handgrip 153 for cooperative releasable and locking engagement with a proximal housing 157 of the trocar cannula 159 of the trocar assembly. The trocar cannula 159, including a tubular cannula 161, is positionable in releasable locking engagement with the obturator 180 of the assembly, with the obturator 180 arranged in generally telescopic relationship coaxially within the tubular cannula 161.

As noted, the obturator 180 is configured generally in accordance with the previously described acoustic assembly 80 of surgical system 10. To this end, the obturator 180 includes a generally elongated transmission rod or waveguide 186 having a distal end effector portion 188. The end effector 188 can be unitary (i.e., one-piece) with the remaining length of the waveguide, or the end effector can be a separate component joined to the elongated waveguide, such as, for example, by a threaded connection or the like. The waveguide 186 is operatively coupled to the transducer assembly 182 by a suitable mounting element 184, whereby ultrasonic energy is transmitted through the waveguide from the transducer assembly.

In the preferred form, elongated waveguide 186 is housed within a generally tubular sheath-like non-vibratory housing positioned generally coaxially about the waveguide 186. In the illustrated embodiment, this preferred arrangement is provided in the form of a plurality of tubular sheath members 220 which carry therein a plurality of compliant isolation supports 216 which function to desirably isolate the tubular sheath members from the ultrasonic energy carried by waveguide 186. The supports 216 thus function in the nature of the supports 116 of the acoustic assembly 80 of previously-described surgical system 10. Tubular members 220 may be assembled by snap-fitment, threaded connection, or other suitable means.

In the illustrated embodiment of the trocar assembly, assembly of the outer sheath-like housing of the distal end portion of the obturator 180 is facilitated by the provision of a pair of sheath portions 221 which fit in cooperating relationship with a coupling member 213. The coupling member 213 may comprise a slit sleeve which cooperatively receives the sheath portions 221, while permitting the distalmost sheath portion 221 to be removed from the coupling member 213, as may be required.

The outer tubular housing of the obturator 180 further includes an interface body 217 which is operatively connected with the distal-most sheath portion 221, again with an isolation support 216 preferably provided for isolating the interface body 217 from the vibratory energy of the internally-positioned waveguide 186.

In use, the ultrasonic obturator 180 of the assembly is positioned telescopically within the tubular cannula 161 of the trocar cannula 159. Locking clips 155 are preferably engaged with the proximal housing 157 of the trocar cannula 159, thus permitting the entire instrument to be readily manipulated as a unit by handgrip 153. With the obturator positioned within the cannula, the free end of the obturator, including end effector 188, projects from the distal end portion of the tubular cannula 161.

Referring now to FIGS. 5, 6, 7, 8, and 8a, diagrammatical views of an interlock 300 configured to be used with the trocar assembly 200 of FIG. 4 are illustrated. The interlock 300 may be coupled to or incorporated into the obturator or the tubular trocar cannula at any suitable location as would be recognized by those skilled in the art. The interlock 300 preferably includes a housing 310, an obturator that includes waveguide 316, braking members 320a and 320b, an arming collar 330, and a reset button 340.

The braking members 320a and 320b are preferably mounted on opposing sides of the waveguide 316. The braking members 320a and 320b are preferably positioned near the proximal end of the waveguide 316. It is contemplated that the braking members 320a and 320b may be positioned at any suitable position along the acoustic assembly. It will be recognized that the interlock 300 may have any suitable number of braking members 320a and 320b, (i.e. 1 to 6) and may be mounted in any suitable arrangement to engage the transmission rod 186.

The braking members 320a and 320b preferably include resilient members 322a and 322b and brake pads 324a and 324b. The brake pads 324a and 324b are preferably of a rectangular configuration. It is also contemplated that the brake pads 324a and 324b may be any shape or size. The braking pads 324a and 324b preferably have a high operating temperature and are constructed so that they will not scratch or gouge the waveguide 316 of the obturator. The braking pads 324a and 324b may be manufactured from polytetra fluoroethylene (PTFE/TFE) or fluorinated ethylene-propylene (FEP). It will be recognized that the braking pads 324a and 324b may be any suitable material known in the art.

The braking pads 324a and 324b preferably include a front surface that conforms to the periphery of the waveguide 316. Preferably, the front surface has a concave surface or groove to receive the waveguide 316. It is contemplated that the front surface of the braking members 320a and 320b may have any desirable configuration and may be substantially flat.

The resilient members 322a and 322b are attached to the rear of the braking members 320a and 320b. The resilient members 322a and 322b bias the braking members 320a and 320b towards the waveguide 316. Preferably, the resilient members 322a and 322b each include a spring. It is also contemplated that the resilient members 322a and 322b may comprise any suitable mechanism to bias the braking members 320a and 320b, such as, for example, a solenoid, a pneumatic piston, etc.

Figure 5:
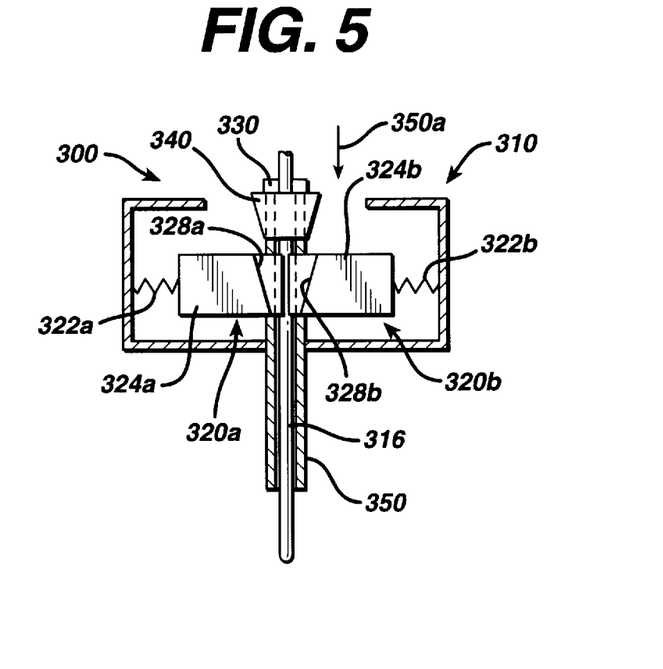
FIG. 5 is a diagrammatical view of an interlock of the ultrasonic trocar assembly of FIG. 4 engaging a transmission component.
Figure 6:
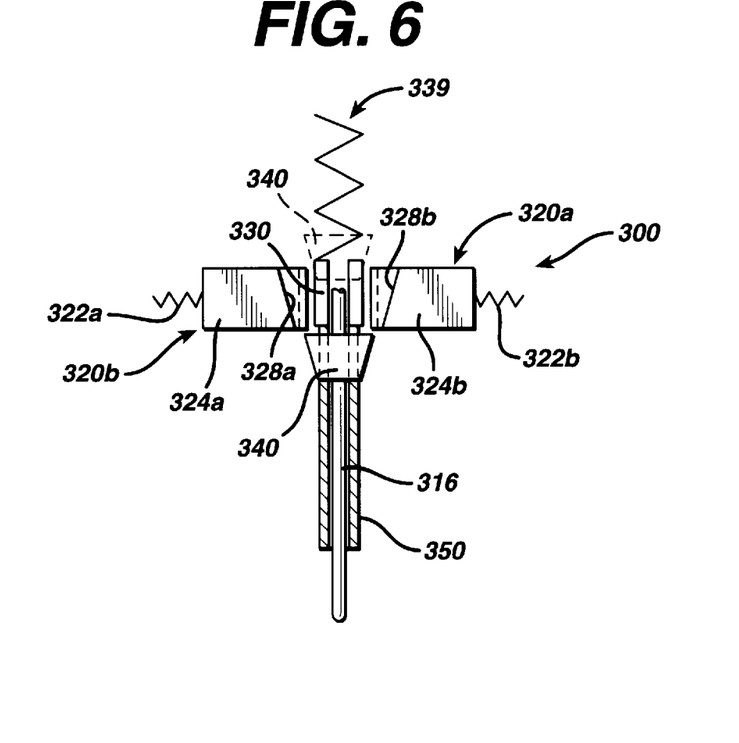
FIG. 6 is a diagrammatical view of the interlock of FIG. 5 disengaged from the transmission component.

The arming collar 330 of the interlock 130 is preferably spring loaded. When the braking members 320a and 320b are depressed against the waveguide 316, the collar 330 is in a retracted position as shown in FIG. 5. Once the braking members 320 and 320b are moved away from the waveguide 316, the collar 330 is preferably disposed between the braking members 320a and 320b as shown in FIG. 6. The arming collar 330 holds the breaking members 320a and 320b away from the waveguide 316. The arming collar 330 is biased by a resilient member 339, such as, for example, a spring.

The braking members 320a and 320b may also include a cam surfaces 328a and 328b. The cam surfaces 328a and 328b are preferably angled inwardly from the proximal end to the distal end. When the reset button 340 is moved in the direction of arrow 350a in FIG. 5, the reset button engages the cam surfaces 328a and 328b and forces the braking members 320a and 320b away from the waveguide 316, as shown in FIG. 6.

The braking members 320a and 320b of the interlock 300 are adapted to engage the periphery of the waveguide 186 at a suitable point or location along the acoustic assembly to dampen or arrest the ultrasonic vibration. The braking members 320a and 320b are preferably applied in the vicinity of an antinode.

Initially, the braking members 320a and 320b are engaged with the waveguide 316, and the reset button 340 is position rearwardly from the braking members 320a and 320b as illustrated in FIG. 5. The interlock 300 is then armed by pushing the reset button 340 forwardly to force the braking member 320a and 320b away from the waveguide 316, as shown in FIG. 6. In this position, the braking members 320a and 320b are held at a predetermined distance away from the waveguide 316 by the arming collar 330. The arming collar 330 is biased into the space between the braking member 320a and 320b by the spring 339. The surgeon may then activate the generator to energize the acoustic assembly.

The trocar assembly is next positioned so that the distal end of the ultrasonic obturator is positioned in contact with the wall of the body cavity to be penetrated. Either prior to or subsequent to such positioning, the ultrasonic system is energized, thereby effecting transmission of ultrasonic energy from a transducer assembly to the distal end of the obturator. By application of suitable pressure via the handgrip 153 (see FIG. 4), the distal end of the obturator can be caused to penetrate the wall of the body cavity as the ultrasonic energy being transmitted through the waveguide acts on the cellular structure of the wall.

Figure 7:
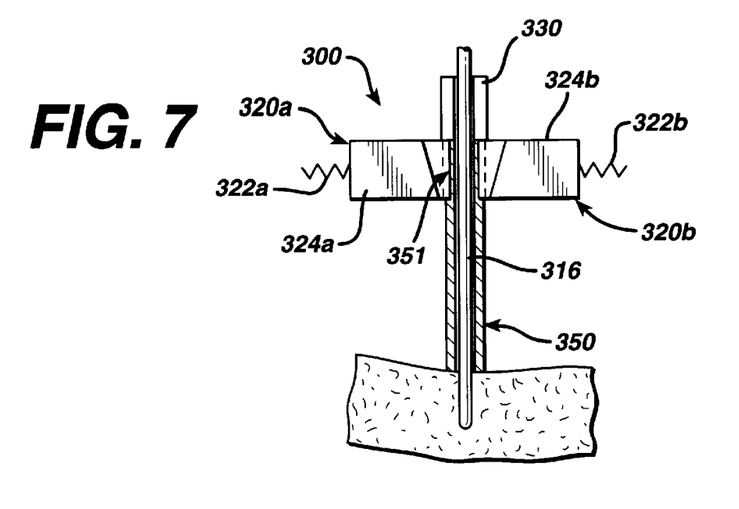
FIG. 7 is a diagrammatical view of the ultrasonic trocar assembly of FIG. 5 having a tissue load sensor in a retracted position.

As shown in FIG. 7, the surgeon begins to press the trocar assembly against the tissue of a patient. As the tissue load sensor 350 retracts, a central post moves into the space between the braking member 320a and 320b from below. As the obturator is advanced into the tissue, the tissue load sensor 350 continues to retract causing the central post to press against the arming collar 330 and moves it out from between the braking members 320a and 320b as illustrated in FIG. 7. Preferably, the center post 351 has a smaller diameter than the arming collar 330, the braking members move slightly inwardly preventing the arming collar 330 from re-engaging but not far enough to engage the waveguide 316 of the obturator. The ultrasonic trocar assembly is then pushed through the tissue and into a cavity, such as the peritoneal.

Figure 8:
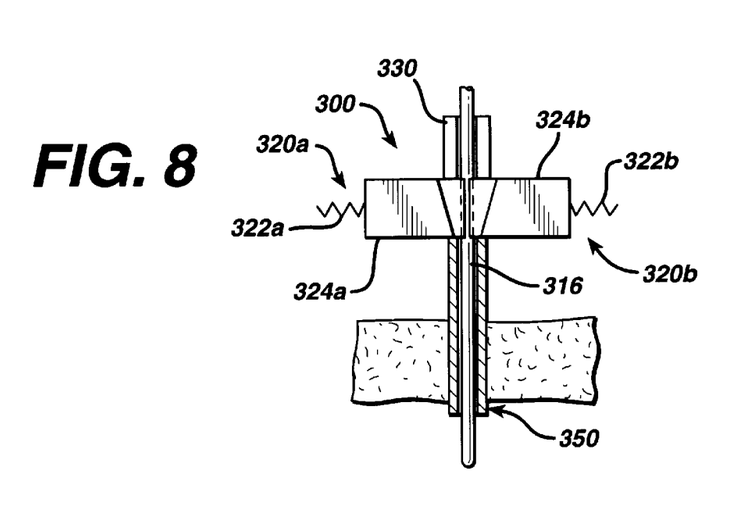
FIG. 8 is a diagrammatical view of the ultrasonic trocar assembly of FIG. 5 having a tissue load sensor in an extended position.
Figure 8A:
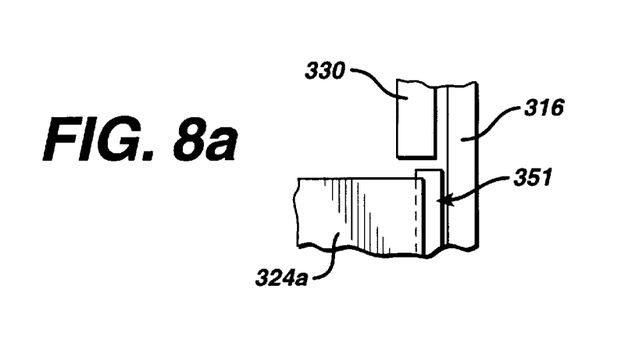
FIG. 8a is an enlarged view of a portion of the interlock of FIG. 7.

When the obturator enters the cavity, the resistance to the tissue load sensor 350 is substantially eliminated and the tissue load sensor 350 is moves forwardly by, for example, a spring (not shown). As the tissue load sensor 350 moves forward, the center post 351 exits the area between the brakes and allows them to contact the waveguide 316. When the braking members 320a and 320b are pushed against the obturator, the braking members 320a and 320b preferably sufficiently increase the impedance of the ultrasonic waveguide so that the generator can no longer lock onto a resonant frequency of the acoustic assembly and produce and adequate drive signal. As a result, the motion of the waveguide ceases, and the generator reports a continuous tone.

After formation of the penetration opening by the ultrasonic obturator, operation of the ultrasonic system can be terminated. The obturator is advanced distally so that the rearwardly and the initially-formed penetration opening becomes sufficiently enlarged as to permit subsequent introduction of the tubular cannula of the trocar cannula. The cannula is then advanced through the dilated and enlarged opening, with the ultrasonic obturator removed prior or subsequent to introduction of the tubular cannula through the enlarged penetration opening. Operation of locking clips permits the obturator to be detached and completely removed from the trocar cannula, and the desired endoscopic surgical procedure performed.

From the foregoing, it will be observed that numerous modifications and variations can be effected without departing from the true spirit and scope of the novel concept of the present invention. It is to be understood that the present disclosure is intended as an exemplification of the invention, and is not intended to limit the invention to the specific embodiment illustrated. The disclosure is intended to cover, by the appended claims, all such modifications as fall within the scope of the claims.

What is claimed is:

1. A method of inserting a trocar cannula into tissue of a patient, comprising the steps of:

providing an ultrasonic trocar obturator having an ultrasonic waveguide including an end effector at a distal end thereof;

positioning the trocar obturator within a trocar cannula;

positioning the trocar obturator in contact with a wall of said body cavity;

ultrasonicly vibrating the end effector to create a penetration opening;

advancing the ultrasonic obturator into said penetration opening;

applying a braking member to the obturator to dampen the ultrasonic vibration of the end effector; and advancing the trocar cannula into the penetration opening.

2. The method of claim 1 further including the step of:

removing the ultrasonic trocar obturator from within the trocar cannula after insertion of said cannula into the penetration opening.

3. The method of claim 1 further including the step of detecting when penetration has been completed.

4. The method of claim 1 further including the step of sensing the impedance of the obturator.

5. A trocar assembly comprising:

a cannula including a cannula handle and a cannula tube extending from the cannula handle;

an obturator adapted to be inserted through the cannula tube, the obturator includes an ultrasonic transducer, a transmission rod, and an end effector wherein the ultrasonic transducer is adapted to vibrate at a selected frequency;

the transmission rod has a first end and a second end, the first end of the transmission rod coupled to the ultrasonic transducer and the second end coupled to the end effector;

a braking device adapted to engage the transmission rod, said braking device including at least one brake pad moveable from a retracted position, to an engaged position in which said brake pad engages said transmission rod to dampen transmission of ultrasonic vibration therethrough; and means for arming said obturator to permit transmission of ultrasonic vibration through said transmission rod to said end effector, said arming means acting in opposition to said braking means to releaseably maintain said braking means out of said engaged position.

6. A trocar assembly in accordance with claim 5, wherein said arming means comprises an arming collar positioned on said transmission rod, said arming collar being movable to position for releasing said braking means as said obturator advances distally of said cannula tube.

* * * * *